United States Patent
Rosen et al.

(10) Patent No.: US 12,245,931 B2
(45) Date of Patent: Mar. 11, 2025

(54) ACHROMATIC LENSES WITH ZONE ORDER MIXING FOR VISION TREATMENT

(71) Applicant: AMO Groningen B.V., Groningen (NL)

(72) Inventors: Robert Rosen, Groningen (NL); Franck Gounou, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 18/542,499

(22) Filed: Dec. 15, 2023

(65) Prior Publication Data

US 2024/0189095 A1     Jun. 13, 2024

Related U.S. Application Data

(63) Continuation of application No. 17/103,935, filed on Nov. 24, 2020, now Pat. No. 11,844,688.

(60) Provisional application No. 62/955,346, filed on Dec. 30, 2019.

(51) Int. Cl.
*A61F 2/16* (2006.01)

(52) U.S. Cl.
CPC .......... *A61F 2/1654* (2013.01); *A61F 2/1618* (2013.01); *A61F 2/1621* (2013.01); *A61F 2/1656* (2013.01); *A61F 2240/001* (2013.01); *A61F 2240/002* (2013.01)

(58) Field of Classification Search
CPC ............................ A61F 2/1654; A61F 2/1656
See application file for complete search history.

(56) References Cited

U.S. PATENT DOCUMENTS

| | | | |
|---|---|---|---|
| 4,655,565 | A | 4/1987 | Freeman |
| 5,071,207 | A | 12/1991 | Ceglio et al. |
| 5,117,306 | A | 5/1992 | Cohen |
| 5,152,787 | A | 10/1992 | Hamblen |
| 5,178,636 | A | 1/1993 | Silberman |
| 5,201,762 | A | 4/1993 | Hauber |
| 5,589,982 | A | 12/1996 | Faklis et al. |
| 5,895,422 | A | 4/1999 | Hauber |
| 6,266,191 | B1 | 7/2001 | Abe |
| 6,366,405 | B2 | 4/2002 | Abe |

(Continued)

FOREIGN PATENT DOCUMENTS

| | | |
|---|---|---|
| CN | 104127263 B | 3/2016 |
| CN | 214761623 U | 11/2021 |

(Continued)

OTHER PUBLICATIONS

Castignoles F., et al., "Comparison of the Efficiency, MTF and Chromatic Properties of Four Diffractive Bifocal Intraocular Lens Designs," Optics Express, Mar. 2010, vol. 18 (5), pp. 5245-5256.

(Continued)

*Primary Examiner* — Javier G Blanco

(57) ABSTRACT

Apparatuses, systems and methods for providing improved ophthalmic lenses, particularly intraocular lenses (IOLs), include features for reducing dysphotopsia effects, such as haloes and glare. Exemplary ophthalmic lenses can include an optic including a diffractive achromat configured to direct light to a common focus, with individual zones of the diffractive achromat directing light to the common focus in at least two different diffractive orders utilizing at least two different diffractive powers.

3 Claims, 7 Drawing Sheets

(56) References Cited

U.S. PATENT DOCUMENTS

| | | |
|---|---|---|
| 6,536,899 B1 | 3/2003 | Fiala |
| 6,590,708 B2 | 7/2003 | Nakai et al. |
| 6,830,332 B2 | 12/2004 | Piers et al. |
| 6,917,472 B1 | 7/2005 | Yun et al. |
| 6,951,391 B2 | 10/2005 | Morris et al. |
| 7,093,938 B2 | 8/2006 | Morris et al. |
| 7,188,949 B2 | 3/2007 | Bandhauer et al. |
| 7,572,007 B2 | 8/2009 | Simpson |
| 7,677,725 B2 | 3/2010 | Piers et al. |
| 7,717,558 B2 | 5/2010 | Hong et al. |
| 8,231,219 B2 | 7/2012 | Weeber |
| 8,292,952 B2 | 10/2012 | Bille |
| 8,529,623 B2 | 9/2013 | Piers et al. |
| 8,623,083 B2 | 1/2014 | Piers et al. |
| 8,709,079 B2 | 4/2014 | Zhang et al. |
| 8,734,511 B2 | 5/2014 | Weeber et al. |
| 8,771,348 B2 | 7/2014 | Zhao |
| 8,992,611 B2 | 3/2015 | Zhao et al. |
| 9,069,185 B2 | 6/2015 | Zhao |
| 9,078,745 B2 | 7/2015 | Zhang et al. |
| 9,089,421 B2 | 7/2015 | Carson et al. |
| 9,122,074 B2 | 9/2015 | Piers et al. |
| 9,223,148 B2 | 12/2015 | Fiala et al. |
| 9,304,329 B2 | 4/2016 | Zhao |
| 9,320,594 B2 | 4/2016 | Schwiegerling |
| 9,335,563 B2 | 5/2016 | Weeber |
| 9,335,564 B2 | 5/2016 | Choi et al. |
| 9,474,595 B2 | 10/2016 | Zhao et al. |
| 9,901,441 B2 | 2/2018 | Barrett et al. |
| 10,175,505 B2 | 1/2019 | Muschielok et al. |
| 10,197,815 B2 | 2/2019 | Weeber et al. |
| 10,226,326 B2 | 3/2019 | Zhao |
| 10,278,811 B2 | 5/2019 | Choi et al. |
| 10,420,638 B2 | 9/2019 | Hong et al. |
| 10,426,599 B2 | 10/2019 | Choi et al. |
| 10,531,950 B2 | 1/2020 | Tiwari et al. |
| 10,588,738 B2 | 3/2020 | Rosen et al. |
| 10,698,234 B2 | 6/2020 | Zhao |
| 10,831,040 B2 | 11/2020 | Dobschal et al. |
| 10,945,834 B2 | 3/2021 | Bor et al. |
| 11,000,361 B2 | 5/2021 | Hong et al. |
| 11,022,815 B2 | 6/2021 | Weeber |
| 2006/0238702 A1 | 10/2006 | Glick et al. |
| 2007/0282438 A1 | 12/2007 | Hong et al. |
| 2008/0147185 A1 | 6/2008 | Hong et al. |
| 2009/0088840 A1 | 4/2009 | Simpson et al. |
| 2009/0210054 A1 | 8/2009 | Weeber et al. |
| 2010/0131060 A1 | 5/2010 | Simpson et al. |
| 2010/0312336 A1 | 12/2010 | Hong et al. |
| 2011/0149236 A1 | 6/2011 | Weeber |
| 2012/0140166 A1 | 6/2012 | Zhao |
| 2014/0005781 A1 | 1/2014 | Zhao et al. |
| 2016/0262876 A1 | 9/2016 | DeBoer et al. |
| 2016/0320633 A1 | 11/2016 | Weeber et al. |
| 2017/0239038 A1 | 8/2017 | Choi et al. |
| 2017/0252151 A1 | 9/2017 | Mackool |
| 2018/0092739 A1 | 4/2018 | Pagnoulle et al. |
| 2018/0147052 A1 | 5/2018 | Hong et al. |
| 2018/0311034 A1 | 11/2018 | Hong et al. |
| 2018/0333255 A1 | 11/2018 | Weeber et al. |
| 2018/0373060 A1 | 12/2018 | Knox et al. |
| 2019/0004335 A1 | 1/2019 | Weeber et al. |
| 2019/0224000 A1 | 7/2019 | Choi et al. |
| 2019/0254810 A1 | 8/2019 | Tiwari et al. |
| 2019/0307557 A1 | 10/2019 | De Carvalho et al. |
| 2019/0314148 A1 | 10/2019 | Liu |
| 2019/0365528 A1 | 12/2019 | Choi et al. |
| 2020/0038172 A1 | 2/2020 | Hussain et al. |
| 2020/0085569 A1 | 3/2020 | Kaschke et al. |
| 2021/0030532 A1 | 2/2021 | Hong et al. |
| 2021/0196450 A1 | 7/2021 | Rosen et al. |
| 2021/0196451 A1 | 7/2021 | Rosen et al. |
| 2021/0196452 A1 | 7/2021 | Gounou et al. |
| 2021/0196453 A1 | 7/2021 | Rosen et al. |
| 2021/0220118 A1 | 7/2021 | Choi et al. |
| 2023/0190452 A1 | 6/2023 | Rosen et al. |
| 2023/0255750 A1 | 8/2023 | Faria Ribeiro et al. |

FOREIGN PATENT DOCUMENTS

| | | |
|---|---|---|
| EP | 0470811 B1 | 9/1997 |
| EP | 2045648 B1 | 4/2012 |
| JP | 2016150213 A | 8/2016 |
| JP | 6504332 B1 | 4/2019 |
| WO | 0241806 A1 | 5/2002 |
| WO | 2006067255 A1 | 6/2006 |
| WO | 2012028755 A1 | 3/2012 |
| WO | 2019130030 A1 | 7/2019 |
| WO | 2020132703 A1 | 6/2020 |

OTHER PUBLICATIONS

Cohen A.L., "Practical Design of a Bifocal Hologram Contact Lens or Intraocular Lens," Applied Optics, Jul. 1, 1992, vol. 31 (19), pp. 3750-3754.

Faklis D., et al., "Spectral Properties of Multiorder Diffractive Lenses", Applied Optics, May 1995, vol. 34 (14), pp. 2462-2468.

Morlock, R., et al., "Patient-Reported Spectacle Independence Questionnaire (PRSIQ): Development and Validation," American Journal of Ophthalmology, Jun. 2017, vol. 178, pp. 101-114.

Sokołowski M., et al. "Hybrid Heptafocal Intraocular Lenses, " Optica Applicata, Dec. 2015, vol. 45 (3), pp. 285-298.

ACHROMATIC LENSES WITH ZONE ORDER MIXING FOR VISION TREATMENT

CROSS-REFERENCE TO RELATED PATENT APPLICATIONS

This application is a continuation of and claims priority to U.S. patent application Ser. No. 17/103,935, filed Nov. 24, 2020, which claims priority to U.S. Provisional Patent Application No. 62/955,346, filed on Dec. 30, 2019, the entire contents of which are hereby incorporated by reference.

BACKGROUND

Embodiments of the present disclosure relate to vision treatment techniques and in particular, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only a limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL."

Monofocal IOLs are intended to provide vision correction at one distance only, usually the far focus. At the very least, since a monofocal IOL provides vision treatment at only one distance and since the typical correction is for far distance, spectacles are usually needed for good vision at near distances and sometimes for good vision at intermediate distances. The term "near vision" generally corresponds to vision provided when objects are at a distance from the subject eye at equal; or less than 1.5 feet. The term "distant vision" generally corresponds to vision provided when objects are at a distance of at least about 5-6 feet or greater. The term "intermediate vision" corresponds to vision provided when objects are at a distance of about 1.5 feet to about 5-6 feet from the subject eye. Such characterizations of near, intermediate, and far vision correspond to those addressed in Morlock R, Wirth R J, Tally S R, Garufis C, Heichel C W D, Patient-Reported Spectacle Independence Questionnaire (PRSIQ): Development and Validation. Am J Ophthalmology 2017; 178:101-114.

There have been various attempts to address limitations associated with monofocal IOLs. For example, multifocal IOLs have been proposed that deliver, in principle, two foci, one near and one far, optionally with some degree of intermediate focus. Such multifocal, or bifocal, IOLs are intended to provide good vision at two distances, and include both refractive and diffractive multifocal IOLs. In some instances, a multifocal IOL intended to correct vision at two distances may provide a near (add) power of about 3.0 or 4.0 diopters.

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive individual zones. When used for ophthalmic lenses these individual zones are typically annular lens zones, or echelettes, spaced about the optical axis of the lens. Each echelette may be defined by an optical zone, a transition zone between the optical zone and an optical zone of an adjacent echelette, and an echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different powers. Together, these echelettes form a diffractive profile.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens. The lenses may also be in the form of a contact lens, most commonly a bifocal contact lens, or in any other form mentioned herein.

Although multifocal ophthalmic lenses lead to improved quality of vision for many patients, additional improvements would be beneficial. For example, some pseudophakic patients experience undesirable visual effects (dysphotopsia), e.g. glare or halos. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. Another area of improvement revolves around the typical bifocality of multifocal lenses. While multifocal ophthalmic lenses typically provide adequate near and far vision, intermediate vision may be compromised.

Improvements may also be found in the field of achromats. Achromatic lenses may be utilized to improve color contrast of a lens, however, if such achromats are provided as diffractive patterns then undesired visual effects may result, such as glare or halos. Improvements in lenses having achromats are thus desired.

BRIEF SUMMARY

Embodiments herein described include ophthalmic lenses including an optic including a diffractive achromat configured to direct light to a common focus, with individual zones of the diffractive achromat directing light to the common focus in at least two different diffractive orders utilizing at least two different diffractive powers. The at least two different diffractive orders may include a 1st diffractive order, and either a 2nd diffractive order or a 3rd diffractive order. The individual zones of the diffractive achromat may be configured to direct light to the common focus in at least three different diffractive orders.

The individual zones of the diffractive achromat may include a plurality of echelettes with a first echelette of the plurality of echelettes having a first width in r-squared space, and a second echelette of the plurality of echelettes having a second width in r-squared space that is different than the first width in r-squared space. The first echelette may have a first step height and the second echelette a second step height that is different than the first step height. The first step height may be proportionate to the first width in r-squared space, and the second step height proportionate to the second width in r-squared space.

The individual zones of the diffractive achromat may each have a different width in r-squared space than other of the individual zones. Each one of the individual zones may have a different step height than other of the individual zones. Each one of the individual zones may have a step height that is proportionate to the width in r-squared space of the respective one of the individual zones.

It is envisioned that any embodiment herein may function as a monofocal optic, an extended depth of focus optic or a multifocal optic.

Embodiments herein described include ophthalmic lenses including an optic including a diffractive achromat including a plurality of echelettes configured to direct light to a common focus, with the plurality of echelettes directing light to the common focus in at least two different diffractive orders utilizing at least two different diffractive powers. A first echelette of the plurality of echelettes may have a first width in r-squared space, and a second echelette of the plurality of echelettes may have a second width in r-squared space that is different than the first width in r-squared space. The first echelette may have a first step height and the second echelette may have a second step height that is different than the first step height. The first step height may be proportionate to the first width in r-squared space, and the second step height proportionate to the second width in r-squared space.

The plurality of echelettes may form a diffractive profile on a first surface of the optic, and each one of the plurality of echelettes may have a different width in r-squared space than other echelettes of the diffractive profile. The plurality of echelettes may be configured to direct light to the common focus in at least three different diffractive orders or in at least four or more different diffractive orders.

Embodiments herein described include a method including fabricating an optic for an ophthalmic lens, the optic including a diffractive achromat configured to direct light to a common focus, with individual zones of the diffractive achromat directing light to the common focus in at least two different diffractive orders utilizing at least two different diffractive powers. The method may further include receiving an ophthalmic lens prescription, and fabricating the optic based on the ophthalmic lens prescription including determining one or more of a diffractive profile of the diffractive achromat or a refractive profile of the optic based on the ophthalmic lens prescription. This method of fabrication may be used to fabricate any lens disclosed herein.

Embodiments herein described include a system for fabricating an ophthalmic lens. The system may include a processor configured to determine at least a portion of a profile of an optic having a diffractive achromat configured to direct light to a common focus, with individual zones of the diffractive achromat directing light to the common focus in at least two different diffractive orders utilizing at least two different diffractive powers. The system may include a manufacturing assembly that fabricates the optic based on the profile. The method may further include an input for receiving an ophthalmic lens prescription, wherein the processor is configured to determine one or more of a refractive profile of the optic or a profile of the diffractive achromat based on the ophthalmic lens prescription. This system for fabricating may be used to fabricate any lens disclosed herein.

The diffractive achromat may be positioned on an anterior or a posterior surface of the optic, or both surfaces. The individual zones of the diffractive achromat configured to direct light to a common focus in a first diffractive order as well as a second (or higher) diffractive order may in be on the same surface of the optic. The diffractive achromat may be combined with extended depth of focus features.

DETAILED DESCRIPTION

FIGS. 1A, 1B, 2A, 2B, 3A and 3B illustrate multifocal IOL lens geometries, aspects of which are described in U.S.

Patent Publication No. 2011-0149236 A1, which is hereby incorporated by reference in its entirety.

Figure 1A:
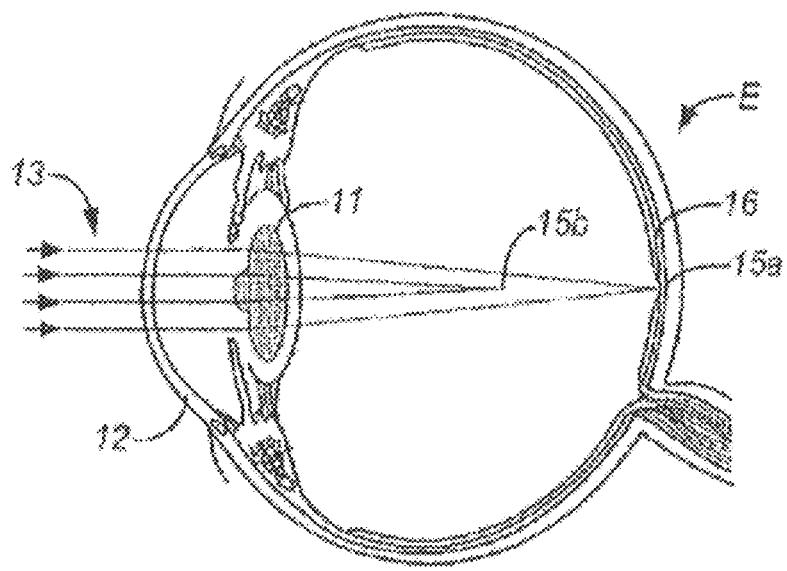
FIG. 1A illustrates a cross-sectional view of an eye with an implanted multifocal refractive intraocular lens.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference and clarity, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens. One or more support elements may be configured to secure the lens 11 to a patient's eye.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
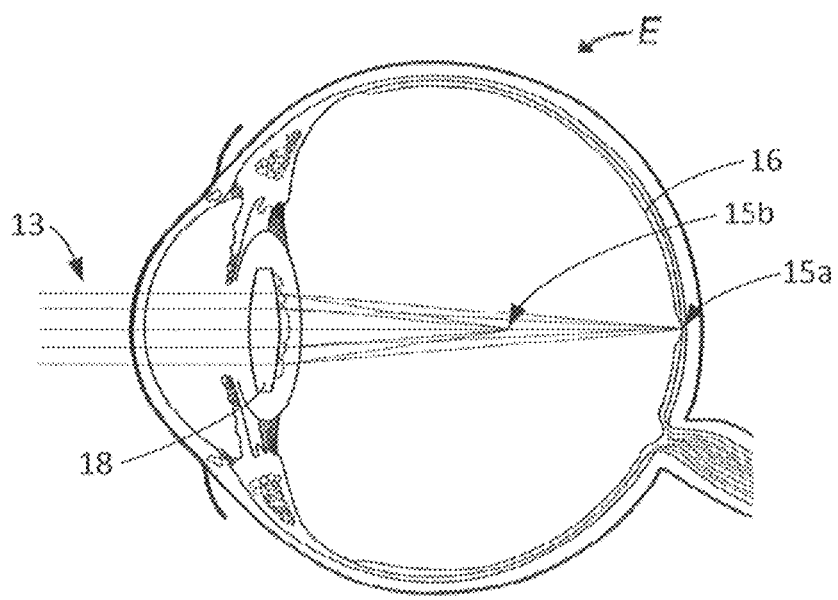
FIG. 1B illustrates a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative power, and that diffractive power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens directs incoming light into a number of diffraction orders. As light 13 enters from the front of the eye, the multifocal lens 18 directs light 13 to form a far field focus 15a on retina 16 for viewing distant objects and a near field focus 15b for viewing objects close to the eye. Depending on the distance from the source of light 13, the focus on retina 16 may be the near field focus 15b instead. Typically, far field focus 15a is associated with 0th diffractive order and near field focus 15b is associated with the 1 st diffractive order, although other orders may be used as well.

Bifocal ophthalmic lens 18 typically distributes the majority of light energy into two viewing orders, sometimes with the goal of splitting imaging light energy about evenly (50%:50%), one viewing order corresponding to far vision and one viewing order corresponding to near vision, although typically, some fraction goes to non-viewing orders.

Corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present disclosure may be applied to inlays, onlays, accommodating IOLs, pseudophakic IOLs, other forms of intraocular implants, spectacles, and even laser vision correction.

Figure 2A:
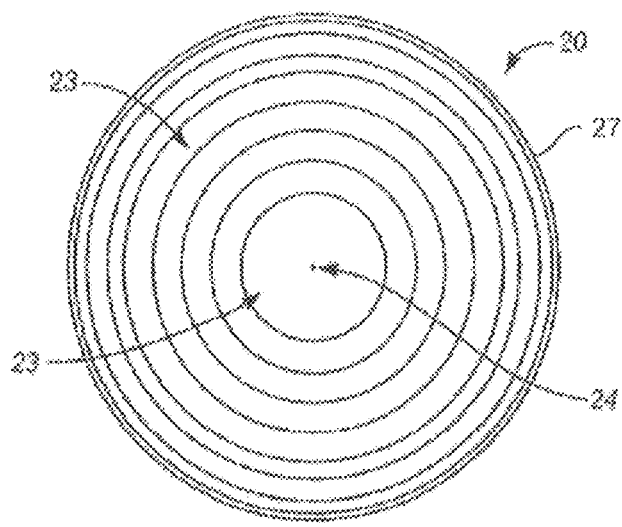
FIG. 2A illustrates a front view of a diffractive multifocal intraocular lens.
Figure 2B:
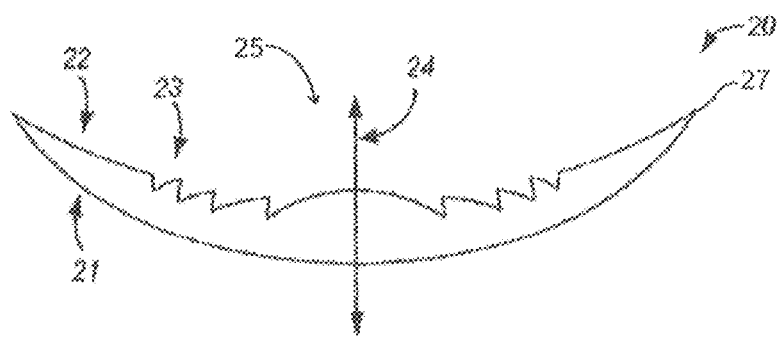
FIG. 2B illustrates a cross-sectional view of a diffractive multifocal intraocular lens.

FIGS. 2A and 2B show aspects of a conventional diffractive multifocal lens 20. Multifocal lens 20 may have certain optical properties that are generally similar to those of multifocal IOLs 11, 18 described above. Multifocal lens 20 has an anterior lens face 21 and a posterior lens face 22 disposed about an optical axis 24. The faces 21, 22, or optical surfaces, extend radially outward from the optical axis 24 to an outer periphery 27 of the optic. The faces 21, 22, or optical surfaces, face opposite each other.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a plurality of annular diffractive individual zones or echelettes 23 spaced about optical axis 24. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano, or other refractive surface combinations.

Figure 3A:
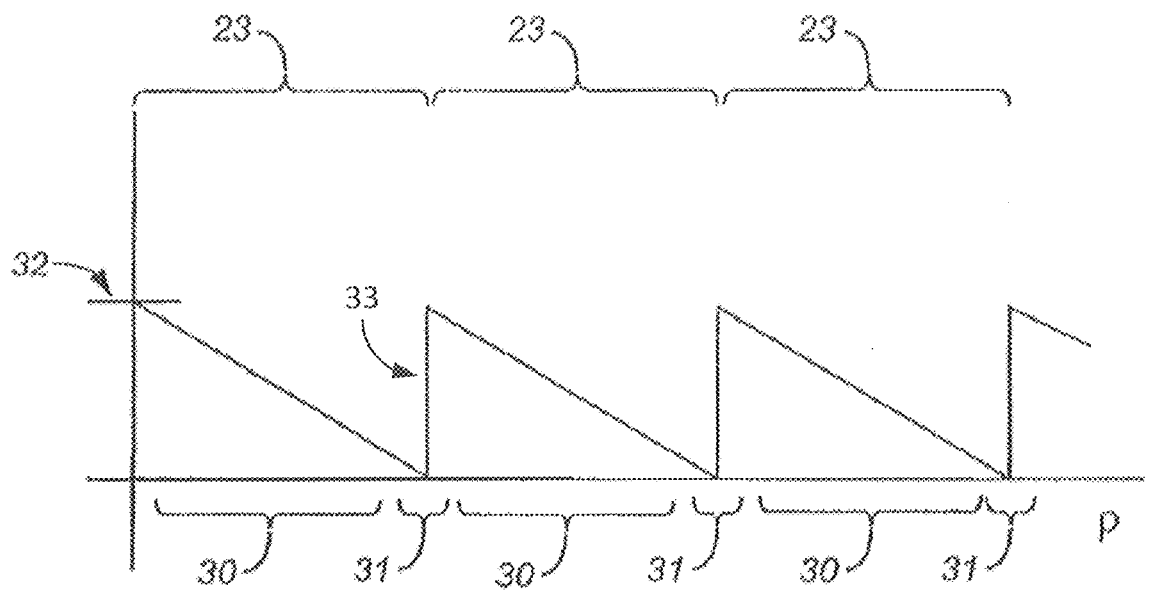
FIGS. 3A-3B are graphical representations of a portion of the diffractive profile of a conventional diffractive multifocal lens.
Figure 3B:
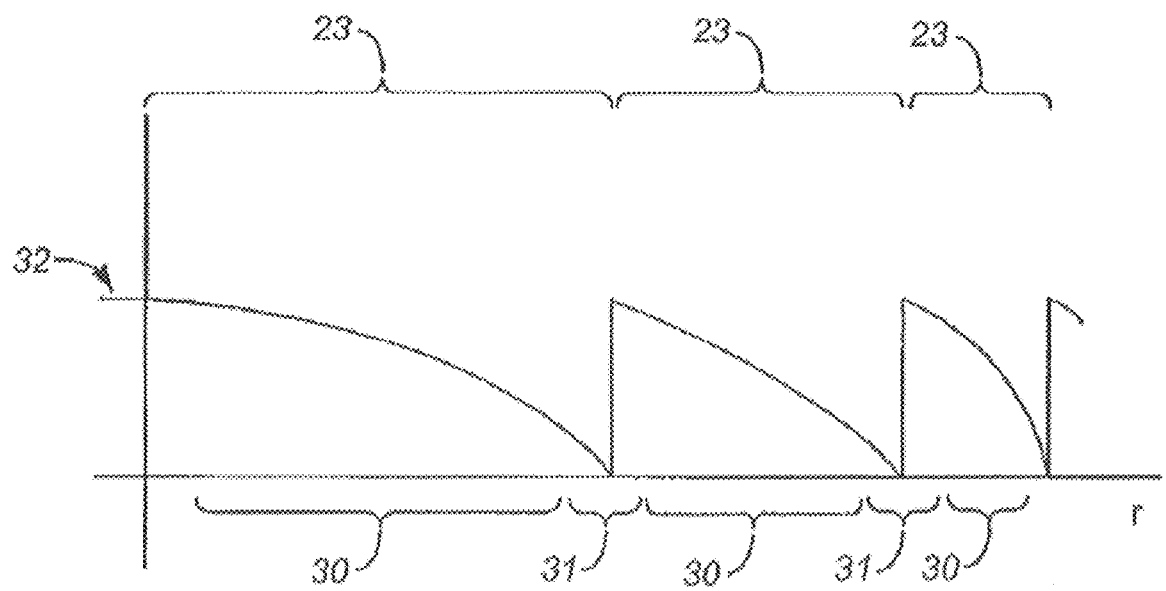

FIGS. 3A and 3B are graphical representations of a portion of a typical diffractive profile of a multifocal lens. While the graph shows only 3 echelettes, typical diffractive lenses extend to at least 9 echelettes to over 32 echelettes. In FIG. 3A, the height 32 of the surface relief profile (from a plane perpendicular to the light rays) of each point on the echelette surface is plotted against the square of the radial distance ($r^2$ or $\rho$) from the optical axis of the lens (referred to as r-squared space). In multifocal lenses, each echelette 23 may have a diameter or distance from the optical axis which is often proportional to $\sqrt{n}$, n being the number of the echelette 23 as counted from optical axis 24. Each echelette has a characteristic optical zone 30 and transition zone 31. Optical zone 30 typically has a shape or downward slope that is parabolic as shown in FIG. 3B. The slope of each echelette in r-squared space (shown in FIG. 3A), however, is the same. As for the typical diffractive multifocal lens, as shown here, all echelettes have the same surface area. The area of echelettes 23 determines the diffractive power of lens 20, and, as area and radii are correlated, the diffractive power is also related to the radii of the echelettes. The physical offset of the trailing edge of each echelette to the leading edge of the adjacent echelette is the step height. An exemplary step height between adjacent echelettes is marked as reference number 33 in FIG. 3A. The step heights remain the same in r-squared space (FIG. 3A) and in linear space (FIG. 3B). The step offset is the height offset of the transition zone from the underlying base curve.

Figure 4:
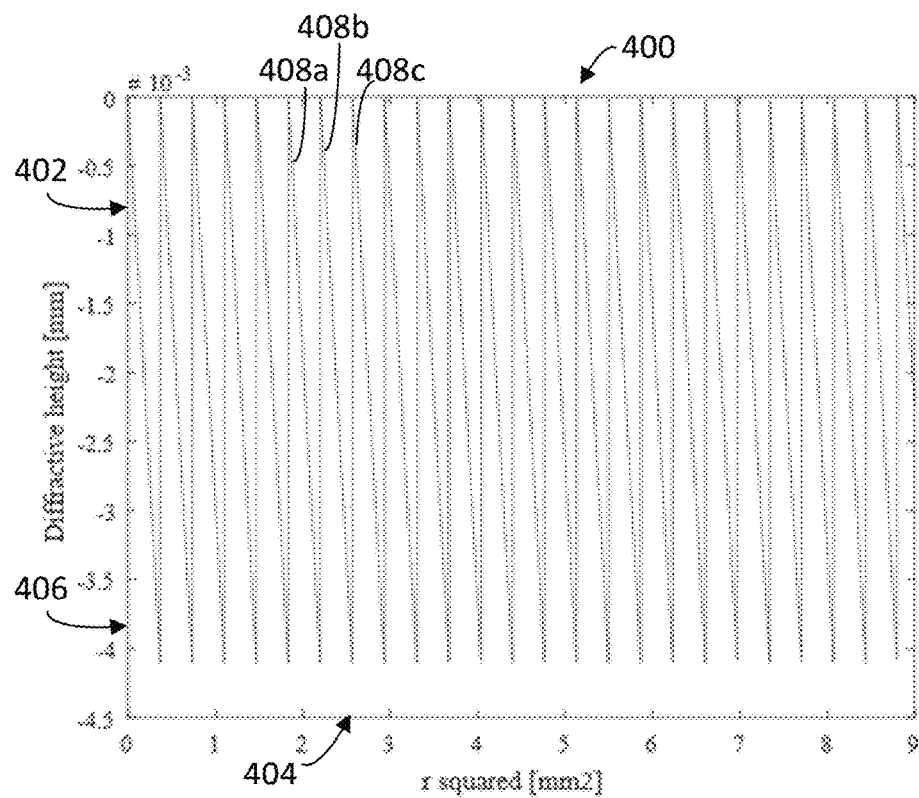
FIG. 4 illustrates a diffractive profile of a diffractive achromat.

Diffractive profiles may be utilized to provide multifocality of lenses and may be utilized to correct chromatic aberrations. A diffractive achromat, including a diffractive profile, may be utilized with an optic to reduce chromatic aberrations. FIG. 4, for example, illustrates a diffractive profile of a diffractive achromat. The diffractive profile 400 of the diffractive achromat is shown relative to the Y axis 402, which represents the phase shift of the diffractive profile 400. The height is shown in units of millimeter (mm), and may represent the distance from the base spherical wavefront generated by the lens. In other embodiments, other units or scalings may be utilized. The height or phase shift of the diffractive profile 400 is shown in relation to the radius on the X axis 404 from the optical axis 406 in r-squared space. The radial coordinate represents the distance from the optical axis 406 in r-squared space, and is shown in units of millimeters squared, although in other embodiments, other units or scalings may be utilized.

The diffractive profile 400 of the diffractive achromat includes a repeating pattern of individual zones or echelettes (representative echelettes 408a, 408b, 408c are marked) that each have the same width in r-squared space. The step height of each echelette is also the same in the diffractive profile 400. The diffractive profile 400 directs light to a focus in a single order, which is typically the 1st diffractive order. Visual symptoms may result from light passing through the transition zones of the echelettes of the diffractive profile 400.

Figure 5:
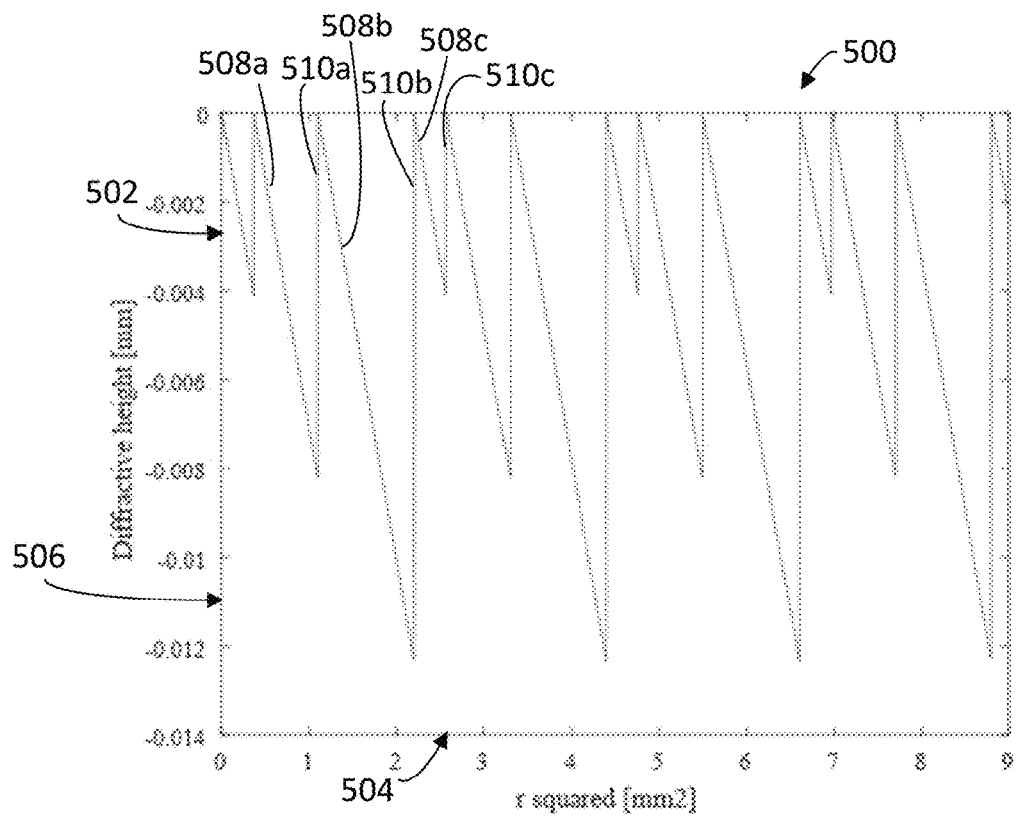
FIG. 5 illustrates a diffractive profile of a diffractive achromat in which the diffractive achromat is configured to direct light to a focus in at least two different diffractive orders.

FIG. 5 illustrates a diffractive profile 500 of a diffractive achromat in which the diffractive achromat is configured to direct light to a common focus, with individual zones of the diffractive achromat directing light to the common focus in at least two different diffractive orders utilizing at least two different diffractive powers. The diffractive achromat is configured to direct light to a common focus for a range of different step heights and zone widths, the combination of which is configured such that all bring light to the same point (common focus), but the diffractive order and power differs between the individual zones. Such a configuration differs from an embodiment as shown in FIG. 4, which directs light to a focus in a single diffractive order with identical step heights. FIG. 5 illustrates the diffractive profile 500 relative to the Y axis 502, which represents the phase shift of the diffractive profile 500. The height is shown in units of millimeters (mm), and may represent the distance from the base spherical wavefront generated by the lens. In other embodiments, other units or scalings may be utilized. The height or phase shift of the diffractive profile 500 is shown in relation to the radius on the X axis 504 from the optical axis 506 in r-squared space. The radial coordinate represents the distance from the optical axis 506 in r-squared space, and is shown in units of millimeters squared, although in other embodiments, other units or scalings may be utilized.

The diffractive profile may include a plurality of individual zones or echelettes (representative echelettes 508a, 508b, 508c are marked) disposed on a surface of an optic. The optic may include an anterior surface and a posterior surface, each disposed about an optical axis, with the anterior surface facing opposite the posterior surface. The diffractive profile may be positioned on an anterior surface or posterior surface, or a combination thereof.

The echelettes 508a, 508b, 508c may each be configured to direct light to a focus in different diffractive orders (at least two different diffractive orders) and different diffractive powers (at least two different diffractive powers) than each other. For example, one of the echelettes 508a, 508b, 508c may be configured to direct light to a focus at a 1st diffractive order, whereas another of the echelettes 508a, 508b, 508c may be configured to direct light to the focus at a 2nd diffractive order, and another of the echelettes 508a, 508b, 508c may be configured to direct light to the focus at a 3rd diffractive order. One diffractive order may be a 1st diffractive order and another diffractive order may be a 2nd or 3rd diffractive order. In embodiments, multiple different combinations of diffractive orders (e.g., 0th, 1st, 2nd, 3rd, 4th, etc.) may be utilized by the diffractive profile to direct light to the focus. The diffractive achromat may be configured to direct light to the focus in at least two different diffractive orders, at least three different diffractive orders, at least four different diffractive orders, or a greater number of orders as desired. The diffractive achromat may be configured to direct light to the focus in at least two different diffractive powers, at least three different diffractive powers, at least four different diffractive powers, or a greater number of powers as desired. Some or all of the echelettes of the diffractive profile 500 may direct light to the focus at different diffractive orders or powers. For example, some of the echelettes of the diffractive profile 500 may repeat on the optic and may direct light to the focus at the same diffractive order and/or power as another of the echelettes of the diffractive profile 500.

The individual zones or echelettes 508a, 508b, 508c may have different step heights to provide varied light distribution at different orders. For example, echelette 508b has a greater step height 510b than echelette 508a (having step height 510a), which has a greater step height than echelette 508c (having step height 510c). To maintain the same focus (or focal length), the echelettes 508a, 508b, 508c may have step heights that are proportionate to the width of the respective echelette 508a, 508b, 508c in r-squared space, as shown in FIG. 5. The widths of the respective echelettes 508a, 508b, 508c may accordingly be different than each other in r-squared space.

By having a diffractive achromat direct light to a focus in a least two different diffractive orders utilizing at least two different diffractive powers, reduced visual symptoms may be provided while chromatic aberration is maintained. Zone order mixing may reduce the visual symptoms present with an embodiment shown in FIG. 4, which directs light to a focus in the same diffractive order.

The diffractive achromat represented in FIG. 5 may be applied to a base optic, which may be a monofocal optic, an extended depth of focus optic, or a multifocal optic, among other types of designs. The optic may be configured to correct for ocular aberrations of a patient's eye, with the diffractive achromat reducing chromatic aberrations. The diffractive achromat may be combined with extended depth of focus features, which may provide for intermediate vision.

Figure 6:
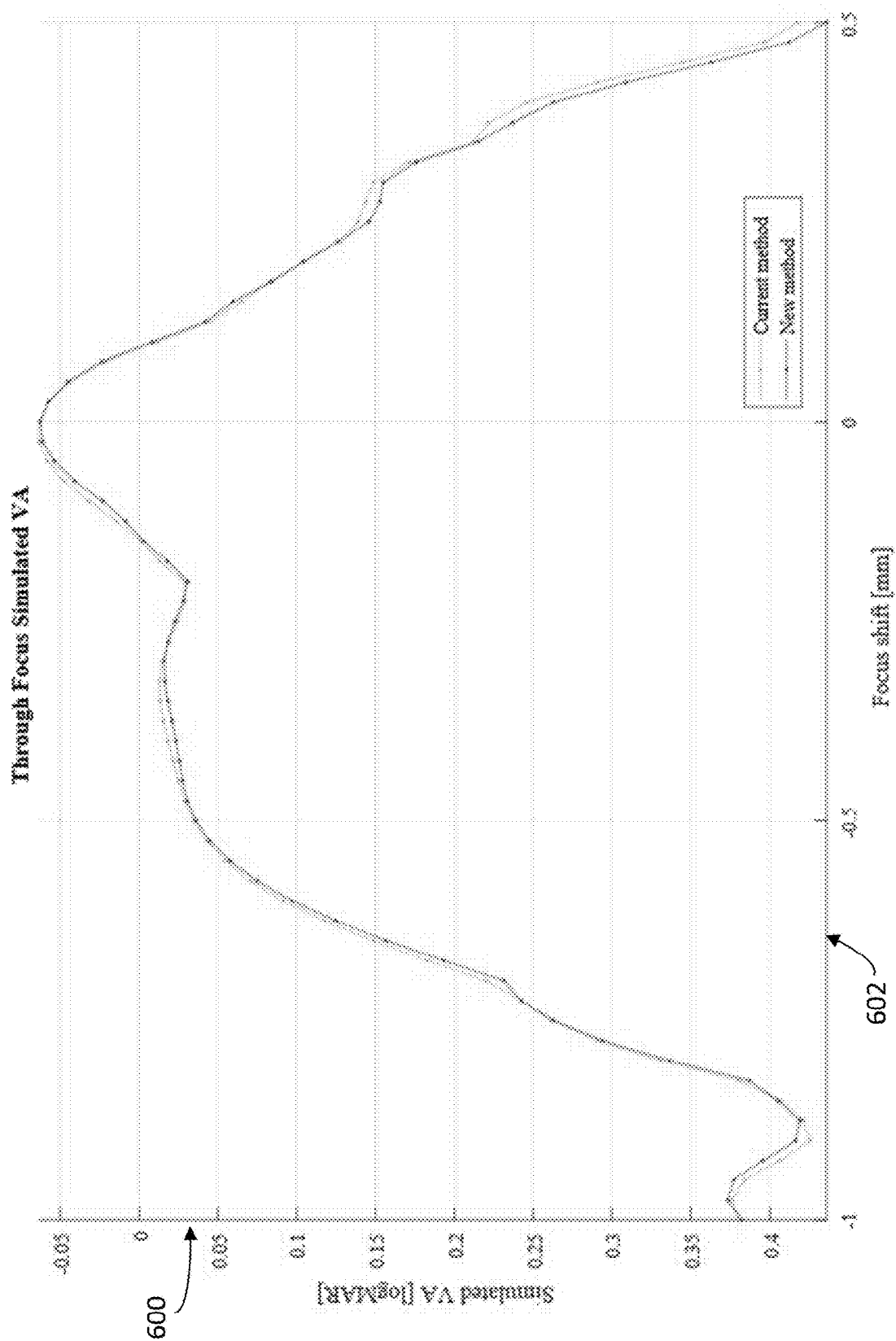
FIG. 6 illustrates a chart of through focus visual acuity (VA) for an extended depth of focus optic that includes a diffractive achromat that directs light to a common focus compared to a similar design with a standard achromat. The performance is the same.
Figure 7:
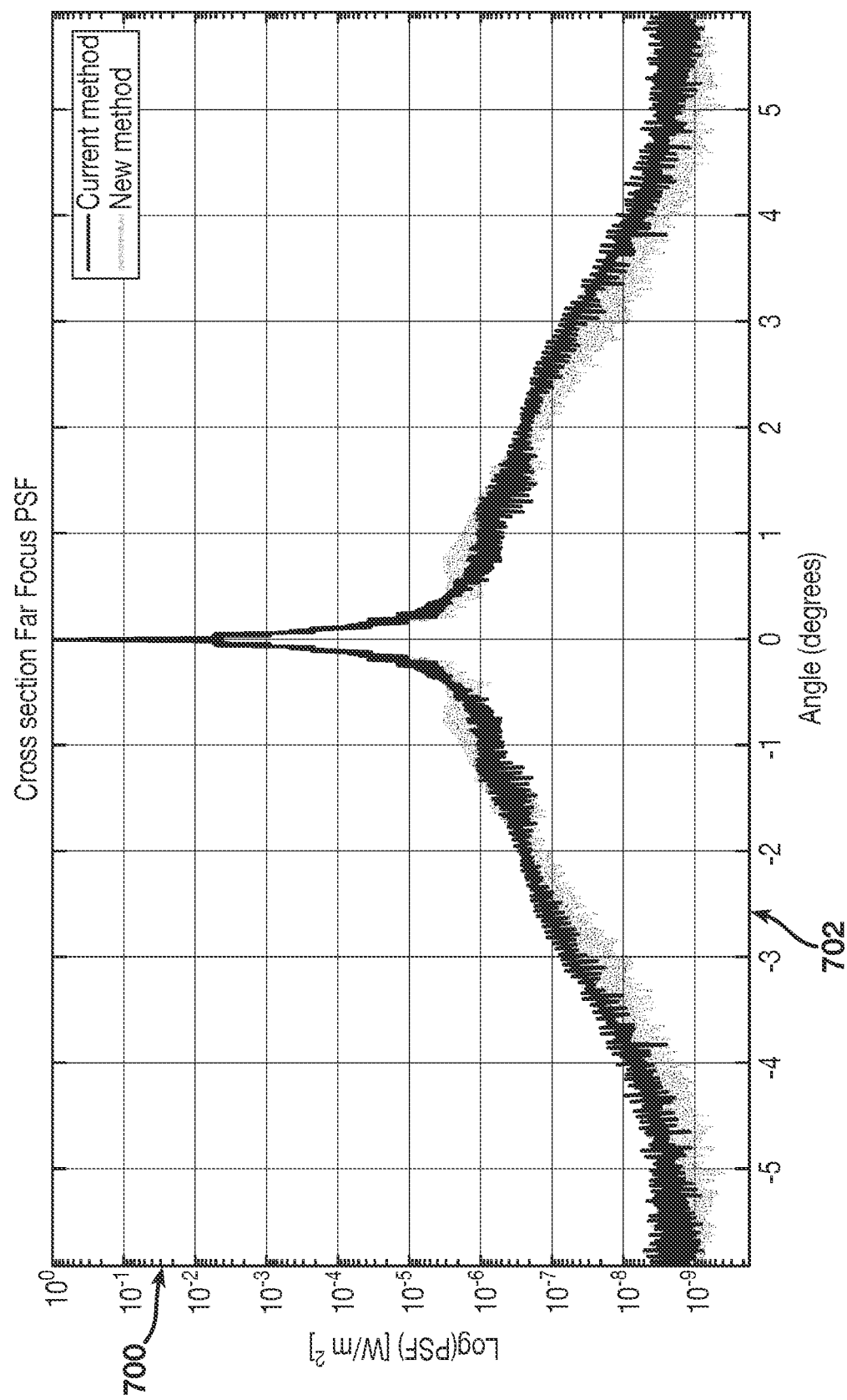
FIG. 7 illustrates a chart of point spread function (PSF) for an extended depth of focus optic that includes a diffractive achromat that directs light to a common focus compared to a similar design with a standard achromat. The performance is better for the achromat of the present disclosure because the decrease in PSF is more gradual.

FIG. 6 illustrates a chart of expected high contrast visual acuity (VA) for an extended depth of focus optic that includes a diffractive achromat that directs light to a focus in a least two different diffractive orders as shown in FIG. 5. VA is shown on the Y axis 600 (as the Logarithm of the Minimum Angle of Resolution), and focus shift in millimeters (mm) is shown on the X axis 602. FIG. 7 illustrates a point spread function (PSF) for such an optic with PSF shown on the Y axis 700 and angle shown on the X axis 702. The scatter profile shows a reduced risk of visual symptoms due to the presence of the diffractive achromat with individual zones that direct light to a common focus in at least two different diffractive orders utilizing at least two different diffractive powers.

An optic for an ophthalmic lens that includes a profile (both the profile of the diffractive and/or a profile of a refractive portion of the optic) disclosed herein may be fabricated utilizing a variety of methods. A method may include determining optical aberrations of a patient's eye. Measurements of a patient's eye may be made in a clinical setting, such as by an optometrist, ophthalmologist, or other medical or optical professional. The measurements may be made via manifest refraction, autorefraction, tomography, or a combination of these methods or other measurement methods. The optical aberrations of the patient's eye may be determined.

The measurements of the patient's eye may be placed in an ophthalmic lens prescription, which includes features of an optic that are intended to address the optical aberrations of the patient's eye.

The ophthalmic lens prescription may be utilized to fabricate an optic for the ophthalmic lens. A refractive profile of the optic may be determined based on the ophthalmic lens prescription, to correct for the optical aberrations of the patient's eye. Such a refractive profile may be applied to the optic. The desired diffractive profile of the diffractive achromat may also be determined. Such a determination may be made based on the desired amount of chromatic aberration to be reduced along with a determination of a desired amount of adverse visual symptoms to be reduced.

The determination of a profile of one or more of the diffractive achromat or a refractive portion of the optic may be performed remotely from the optometrist, ophthalmologist, or other medical or optical professional that performed the measurements of a patient's eye, or may be performed in the same clinical facility of such an individual. If performed remotely, the fabricated optic may be delivered to an optometrist, ophthalmologist, or other medical or optical professional, for being provided to a patient. For an intraocular lens, the fabricated optic may be provided for implant into a patient's eye.

The fabricated optic may be a custom optic fabricated specifically for the patient's eye, or may be fabricated in a manufacturing assembly and then selected by an optometrist, ophthalmologist, or other medical or optical professional for supply to a patient, which may include implantation in the patient's eye.

Figure 8:
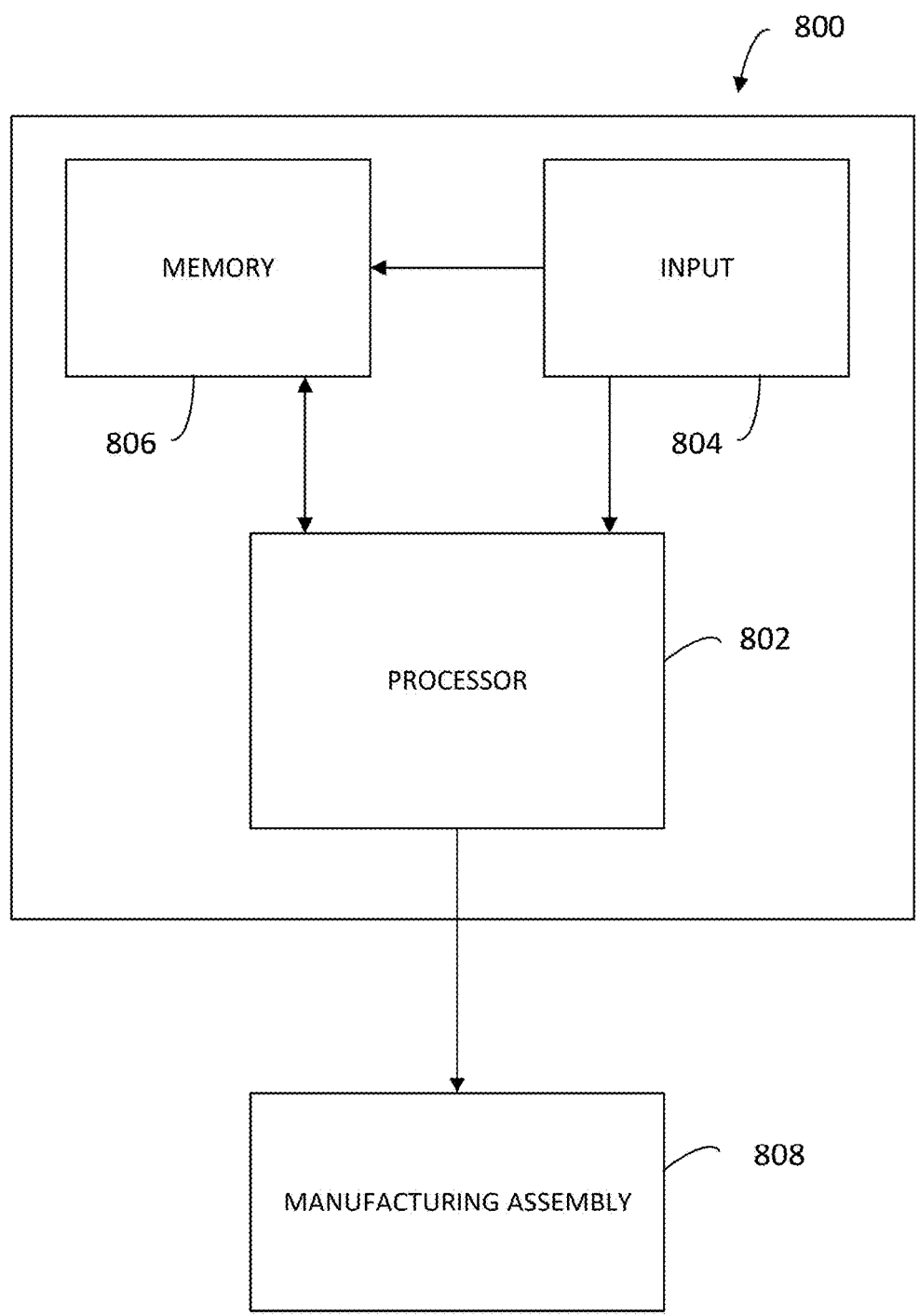
FIG. 8 illustrates an embodiment of a system.

FIG. 8 illustrates an embodiment of a system 800 that may be utilized to perform all or a portion of the methods disclosed herein. The system 800 may include a processor 802, an input 804, and a memory 806. In certain embodiments the system 800 may include a manufacturing assembly 808.

The processor 802 may comprise a central processing unit (CPU) or other form of processor. In certain embodiments the processor 802 may comprise one or more processors. The processor 802 may include one or more processors that are distributed in certain embodiments, for example, the processor 802 may be positioned remote from other components of the system 800 or may be utilized in a cloud computing environment. The memory 806 may comprise a memory that is readable by the processor 802. The memory 806 may store instructions, or features of intraocular lenses, or other parameters that may be utilized by the processor 802 to perform the methods disclosed herein. The memory 806 may comprise a hard disk, read-only memory (ROM), random access memory (RAM) or other form of non-transient medium for storing data. The input 804 may comprise a port, terminal, physical input device, or other form of input. The port or terminal may comprise a physical port or terminal or an electronic port or terminal. The port may comprise a wired or wireless communication device in certain embodiments. The physical input device may comprise a keyboard, touchscreen, keypad, pointer device, or other form of physical input device. The input 804 may be configured to provide an input to the processor 802.

The system 800 may be utilized to perform the methods disclosed herein, such as the processes of determining a profile of one or more of the diffractive achromat or a refractive portion of the optic.

The processor 802 may provide the profile of one or more of the diffractive achromat or a refractive portion of the optic to the manufacturing assembly 808, which may be configured to fabricate the optic for the ophthalmic lens based on the profile of one or more of the central refractive region or the diffractive achromat. The manufacturing assembly 808 may comprise one or more apparatuses for forming the optic, and may comprise a high volume manufacturing assembly or a low volume manufacturing assembly. The manufacturing assembly 808 may be used for manufacture remote to a clinic in which measurements of the individual's eye or made, or local to such a clinic. The manufacturing assembly may include apparatuses such as lathe tools, or other lens formation devices to fabricate the optic.

In one embodiment, the processor 802 may be provided with an ophthalmic lens prescription for the individual's eye that may be provided as discussed herein. The processor 802 may receive the ophthalmic lens via the input 804. The system 800 may fabricate the optic for the ophthalmic lens based on the prescription.

The system 800 may be configured to fabricate any of the embodiments of ophthalmic lenses disclosed herein.

In one embodiment, a profile as shown in FIG. 5 may be positioned on a surface of a lens that is opposite an aspheric surface. The aspheric surface on the opposite side of the lens may be designed to reduce corneal spherical aberration of the patient.

In one embodiment, one or both surfaces of the lens may be aspherical, or include a refractive surface designed to extend the depth of focus, or create multifocality.

Any of the embodiments of lens profiles discussed herein may be apodized to produce a desired result. The apodization may result in the step heights and step offsets of the echelettes being gradually varied according to the apodization, as to gradually increasing the amount of light in the distance focus as a function of pupil diameter.

The features of the optics disclosed herein may be utilized by themselves, or in combination with refractive profiles of the optics and/or with other features providing for correction of chromatic aberrations.

The ophthalmic lenses disclosed herein in the form of intraocular lenses are not limited to lenses for placement in the individual's capsular bag. For example, the intraocular lenses may comprise those positioned within the anterior chamber of the eye. In certain embodiments the intraocular lenses may comprise "piggy back" lenses or other forms of supplemental intraocular lenses.

Features of embodiments may be modified, substituted, excluded, or combined as desired.

In addition, the methods herein are not limited to the methods specifically described, and may include methods of utilizing the systems and apparatuses disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method comprising:
receiving an intraocular lens prescription; and
fabricating an optic for an intraocular lens, based on the intraocular lens prescription,
wherein the optic comprises a diffractive achromat configured to direct light to a common focus, with individual zones of the diffractive achromat directing light to the common focus in at least two different diffractive orders utilizing at least two different diffractive powers,
wherein the individual zones of the diffractive achromat comprise a plurality of echelettes comprising a first echelette of the plurality of echelettes having a first width in r-squared space, and second echelette of the plurality of echelettes having a second width in r-squared space that is different than the first width in r-squared space.

2. The method of claim 1, further comprising determining one or more of a diffractive profile of the diffractive achromat or a refractive profile of the optic based on the intraocular lens prescription.

3. The method of claim 1, wherein the diffractive achromat is configured to direct light to the common focus in at least three different diffractive orders.

* * * * *